United States Patent [19]

de Cooker et al.

[11] 4,109,089

[45] Aug. 22, 1978

[54] METHOD OF PREPARING CYANURIC ACID

[75] Inventors: Mario G. R. T. de Cooker, Sittard; Antonius J. M. Hermus, Eindhoven, both of Netherlands

[73] Assignee: Stamicarbon, B.V., Geleen, Netherlands

[21] Appl. No.: 834,663

[22] Filed: Sep. 19, 1977

[30] Foreign Application Priority Data

Sep. 23, 1976 [NL] Netherlands ............... 7610557

[51] Int. Cl.² ........................................... C07D 251/32
[52] U.S. Cl. ................................................... 544/192

[58] Field of Search ........................................ 544/192

[56] References Cited

U.S. PATENT DOCUMENTS 3,956,299  5/1976  Otter et al. ..................... 544/192

Primary Examiner—John M. Ford
Attorney, Agent, or Firm—Cushman, Darby & Cushman

[57] ABSTRACT

An improved process for preparing cyanuric acid by heating urea or biuret or a mixture thereof in a solvent to produce a cyanuric acid product of high purity.

9 Claims, 1 Drawing Figure

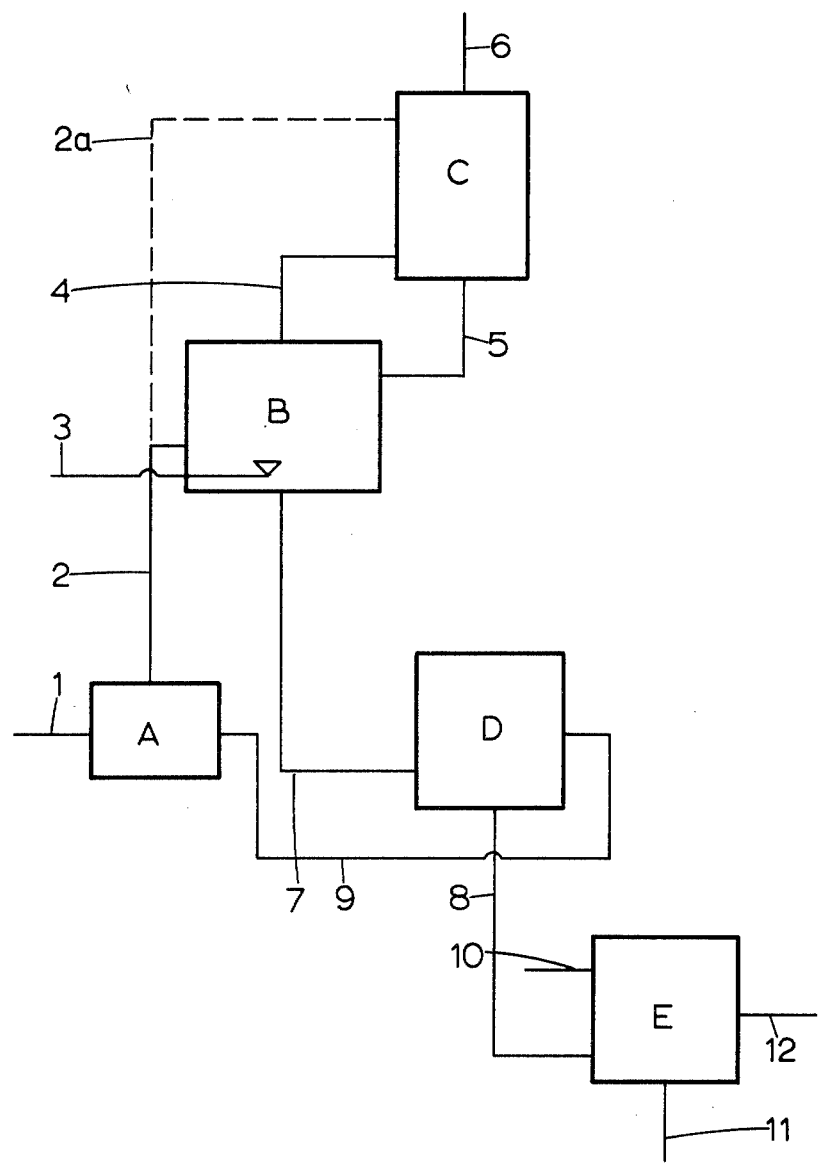

METHOD OF PREPARING CYANURIC ACID

BACKGROUND OF THE INVENTION

This application is related to Netherlands Patent Application No. 7610557, filed Sept. 23, 1976, the entire disclosure of which is hereby incorporated by reference.

The present invention relates to a process for preparing cyanuric acid by heating urea, biuret or a mixture of urea and biuret in a solvent to produce a pure cyanuric acid product with a low content of the by-products ammelide and ammeline.

Cyanuric acid is used as an intermediate in the preparation of other chemical compounds, e.g., the preparation of chlorocyanuric acid which is used in dry bleach compositions and detergents by direct chlorination of cyanuric acid in alkaline solution, and the production of resins.

The production of cyanuric acid from urea or biuret is known. The basic steps consist of first heating urea or biuret for several hours. This results in deamination of the urea and the formation of cyanuric acid:

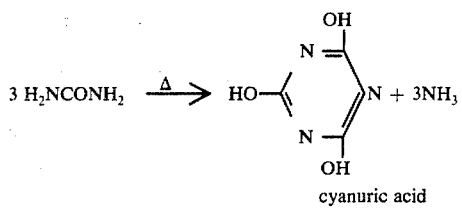

cyanuric acid

The reaction, however, is not as simple as the equation suggests. When urea or biuret is heated, it goes through several states before it is converted to cyanuric acid. Initially, the starting material melts to form a freeflowing liquid. As the heating continues, the reaction mass thickens and finally solidifies. However, at this point, the reaction is not complete. The reaction mass still contains significant amounts of urea, biuret, and triuret, which require additional heating to convert them to cyanuric acid. The additional heating is difficult because of the poor heat-transfer characteristics of the reaction mass. If the reaction mass is heated to too high a temperature, the yield of cyanuric acid product decreases due to depolymerization of the product. Another problem with the reaction is that the reaction product strongly adheres to the walls of the reactor and is removed with great difficulty.

Several methods have been proposed to overcome these problems. For example, it has been proposed to run the reaction in certain high-boiling organic solvents. This and other proposed methods of overcoming the above-discussed problems are mentioned in the article "Triazinetriol" in the *Kirk-Othmer Encyclopedia of Chemical Technology, Second Edition,* Volume 20, pages 662 to 671, the entire disclosure of which is hereby incorporated by reference.

Many organic solvents have been proposed for use in running the reaction to convert urea or biuret to cyanuric acid. Examples of solvents which have been proposed include tetra (lower) alkyl ureas such as tetramethyl urea and tetraethyl urea; phenolic solvents such as cresol, xylenol, and chlorocresols; substituted amides such as dimethylformamide, dibutylformamide, and dimethylacetamide; glycol ethers; and methanes such as 5-methyl-2-oxazolidinone. The use of such solvents is disclosed in Netherlands Patent Application No. 74.05629 which is available for public inspection. However, each of the proposed organic solvents has its own disadvantages, particularly the presence of organic impurities in the cyanuric acid product.

It is a particular disadvantage of prior processes that the organic impurities produced in the cyanuric acid product are difficult to remove. However, the removal of such organic impurities is required for various applications of cyanuric acid. For example, ammeline and ammelide are formed as by-products in the preparation of cyanuric acid from urea, and are considered impurities in the cyanuric acid product. Typically, prior processes for preparing cyanuric acid from urea using no solvent produce as much as 20-30% impurities consisting mostly of ammelide and ammeline, with minor amount of melamine, biuret, urea and triuret (*Kirk-Othmer Encyclopedia*, supra). Ammeline and ammelide are very undesirable by-products because they interfere in some important applications of cyanuric acid. Consequently, the ammeline and ammelide content of cyanuric acid may be required to be less than 1% by weight. It is common practice to purify crude cyanuric acid containing ammeline and ammelide by treating the crude acid with a strongly acid aqueous solution, so that the ammeline and ammelide are hydrolyzed into cyanuric acid. However, such a hydrolysis step is expensive, so that it would be very desirable to avoid it. Cyanuric acid obtained by prior out processes wherein an organic solvent is used contains normally besides ammelide and ammeline also traces of the solvent as organic impurities which are difficult to remove.

An advantageous method of preparing cyanuric acid from urea or biuret or mixtures thereof has been discovered wherein ammonium nitrate is used as a solvent.

It is known from U.S. Pat. No. 2,949,848 that guanidine nitrate can be obtained by heating a liquid mixture of urea and ammonium nitrate at a temperature of 175° to 225° C. in the presence of a silica catalyst such as silica gel. The ammonium nitrate is used as a reactant with urea in this reaction. Therefore, one would not expect a melt containing ammonium nitrate to be a suitable solvent for urea in the production of cyanuric acid.

It is also known from Zhur. Prikl. Khim. 37, pages 1158-60 (1964) to prepare cyanuric acid by heating a urea melt in the absence of a solvent, but in the presence of a subordinate amount of ammonium nitrate. The ammonium nitrate is used as a quasi catalyst and not as a solvent. In such a process, the yield of cyanuric acid is very poor.

SUMMARY OF THE INVENTION

Briefly, in accordance with the invention, cyanuric acid is prepared by heating urea or biuret or a mixture thereof in molten ammonium nitrate as a solvent in the absence of any silica catalyst. The methode of the present invention is further characterized by reduction of the concentration in the reactor of the ammonia produced with the cyanuric acid from the reaction vessel and by keeping the concentration of urea and/or biuret in the said solvent below 500 grams per kg of solution. It is a particular advantage of the method of the present invention that it produces with a high yield a pure cyanuric acid product with a low content of the by-products ammelide and ammeline and of guanidine nitrate.

It is therefore an object of the present invention to provide a method of preparing cyanuric acid by heating urea or biuret or a mixture thereof in a molten ammonium nitrate solvent in the absence of any silica catalyst to produce cyanuric acid with a low content of guanidine nitrate.

Another object of the present invention is to provide a method of preparing cyanuric acid by heating urea or biuret or a mixture thereof in a molten ammonium nitrate solvent in the absence of any silica catalyst to produce with a high yield cyanuric acid with a low content of ammelide and ammeline.

Another object of the present invention is to provide a method of preparing cyanuric acid by heating urea or biuret or a mixture thereof in a molten ammonium nitrate solvent containing up to 50% by weight of one or more other salts such as an alkali or alkaline earth metal salt.

Another object of the present invention is to provide a method of preparing cyanuric acid by heating urea or biuret or a mixture thereof in a molten ammonium nitrate solvent containing up to 50% by weight of an alkali or alkaline earth metal nitrate, or a mixture of such nitrates.

Other objects of the present invention will be apparent from the description of the invention which follows.

DESCRIPTION OF THE DRAWING

The process according to the present invention may be carried out either batchwise, or continuously. The drawing illustrates an example of a continuous process according to the invention.

Urea or biuret or a mixture thereof is passed through conduit 1 into dissolving vessel A, in which the urea, biuret or a mixture thereof is dissolved in a molten ammonium nitrate solvent in the absence of any silica catalyst. The resulting solution flows through conduit 2 to reaction vessel B, which is a gas-liquid contactor where the conversion into cyanuric acid is effected. In the process according to the present invention it is advantageous to lower the ammonia concentration in reaction vessel B. This may be done in any known way. For example, a non-condensable stripping gas such as nitrogen or carbon dioxide, or a condensable stripping additive such as xylene, or a mixture thereof, may be fed to reaction vessel B through conduit 3. A gaseous mixture containing ammonia, which is produced together with cyanuric acid, and ammonium nitrate vapor, leaves reaction vessel B through conduit 4 and is fed to condenser C. The gaseous mixture leaving reaction vessel B may also contain vapors of stripping gas (e.g., xylene), if one is used.

Condenser C will condense any ammonium nitrate vapor and condensable stripping gas present in the gaseous mixture, and return them to reaction vessel B through conduit 5. Condenser C may also be a scrubber, in which the scrubbing liquid is preferably a solution of urea, or biuret, or a mixture thereof in the molten solvent used. When condenser C is a scrubber, the scrubbing solution is supplied to condenser C through conduit 2a. The vapors of ammonium nitrate, as well as vapors of any other volatile salts can also be washed from the gaseous mixture by means of an aqueous liquid, such as water. Any ammonia which is removed by the washing liquid can be recovered by desorption, e.g., by stripping.

Uncondensed gas escapes from condenser C through conduit 6. This gas consists of substantially pure ammonia or of a mixture of ammonia and stripping gas from which the ammonia can readily be recovered.

A suspension of cyanuric acid in molten salt flows from reactor vessel B through conduit 7 to separator D. In separator D, the cyanuric acid is separated from the molten salt by filtration, precipitation, decantation, centrifugation, or by another suitable separatory method. The solid cyanuric acid product is passed through conduit 8 to washer E, where it is washed with washing liquid supplied through conduit 10. The washing liquid used may, for example, be water, which leaves washer E through conduit 11. The washing liquid leaving washer E contains solvent salt(s), unconverted urea and/or biuret, and some cyanuric acid. If desired, these substances can be separated from the washing liquid and returned to the reaction system. Pure cyanuric acid is discharged through conduit 12.

If desired, the solid cyanuric acid product leaving separator D through conduit 8 may be subjected to a conventional acid hydrolysis, e.g., with nitric acid, in order to hydrolyze the by-products ammelide and ammeline into cyanuric acid. The hydrolyzed cyanuric acid product continues to pass through conduit 8 to washer E, where it is treated as described above. In the practice of the present invention, however, hydrolysis will not generally be necessary since the ammeline and ammelide content of the cyanuric acid product is already low enough for almost all applications.

The mother liquor which is separated in separator D from the solid cyanuric acid product often still contains unconverted urea and/or biuret, and is saturated with cyanuric acid. This mother liquor is passed through conduit 9 to dissolving vessel A.

At the beginning of the continuous process, a given amount of molten salt is put in reactor vessel B. This molten salt solvent keeps recycling, and any losses may be made up through conduits (not shown) located in the system, preferably at dissolving vessel A.

DETAILED DESCRIPTION OF THE INVENTION

The present invention provides a process for preparing cyanuric acid by heating urea or biuret or a mixture thereof in a molten ammonium nitrate solvent. The molten ammonium nitrate solvent according to the present invention is free of any silica catalyst. The molten ammonium nitrate solvent may also contain a minor amount of another salt, e.g., an alkali or alkaline earth metal salt or an ammonium salt. In accordance with the present invention, this "minor amount" of another salt is at most 50% by weight of another salt.

Salts of sodium and potassium are particularly suitable alkali metal salts for use as the other salt in the present invention, although other alkali metal salts, such as salts of lithium, may also be used. Salts of magnesium and calcium are particularly suitable alkaline earth metal salts for use as the other salt in the present invention, although salts of other alkaline earth metals such as strontium and barium may also be used in the practice of the present invention. The salts may be derived for example from hydrochloric acid, sulphuric acid, phosphoric acid, an organic acid (preferably an alifatic carboxylic acid, particularly a fatty acid with up to 18 carbon atoms per molecule), or preferably nitric acid. Preferably the salts used to form the molten salt solvent in the practice of the present invention are free of water.

As used in the present application, the alkali metals include the elements of Group 1a of the "Periodic Table of the Elements" published in the *Handbook of Chemistry & Physics, 47th Ed.*, except hydrogen, and the alkaline earth metals are the elements of group 2a of the same "Periodic Table of the Elements".

Examples of salts which are especially suitable for use in the practice of the present invention as additional components of the molten ammonium nitrate solvent include sodium nitrate, potassium nitrate, calcium nitrate, mixtures of sodium and potassium nitrate, mixtures of sodium nitrate, potassium nitrate and calcium nitrate, etc. It is preferred that the salt mixtures have, at least approximately, the eutectic composition. The additional components of the molten solvent may inhibit undesirable thermal decomposition of ammonium nitrate. It is preferred that the molten ammonium nitrate solvent of the present invention contain from about 10% by weight to about 40% by weight based on the weight of ammonium nitrate of an additional salt as described above In the process according to the present invention, it is advantageous to lower the ammonia concentration in reaction vessel B, i.e., the reaction vessel in which the conversion into cyanuric acid is effected. It will be remembered that the conversion of three moles of urea produces one mol of cyanuric acid and three moles of ammonia. The ammonia concentration may be reduced in the reaction vessel B by any known method. For example, the ammonia concentration may be lowered by stripping by means of a stripping gas such as air, nitrogen or carbon dioxide. Use may also be made of stripping or boiling additives that are fed to the reactor in the liquid state such as aliphatic, aromatic or mixed aliphatic-aromatic hydrocarbons. Suitable liquid stripping or boiling additives include hydrocarbons containing from about 3 to about 12 carbon atoms per molecule, such as cyclohexane, toluene, or a xylene. The ammonia concentration in the reactor may also be lowered by reducing the pressure above the reaction system, i.e., by conducting the conversion to cyanuric acid under less than atomspheric pressure.

The reaction temperature, i.e., the temperature at which urea, biuret or a mixture thereof is converted into cyanuric acid in a molten salt solvent in the practice of the present invention, usually ranges between about 150° C and about 280° C., preferably between about 170° C. and about 220° C., and most preferably between about 175° C. and about 200° C. As the reaction temperature is raised, the reaction proceeds more quickly. However, as the reaction temperature is raised, the amount of undesired by-products, such as ammelide and ammeline, increases. Furthermore, increasing the reaction temperature increases the rate of decomposition of the molten ammonium nitrate solvent used in the process of the present invention.

The reaction pressure used in the practice of the present invention may range between about 0.01 and about 10 atmospheres. Preferably, the reaction pressure used in the practice of the present invention is between about 0.5 and about 2 atmospheres. Most preferably, the reaction pressure used in the practice of the present invention is approximately atmospheric pressure. When the ammonia concentration in the reaction vessel is lowered by conducting the reaction at less than atmospheric pressure, it is preferred to use a reaction pressure between about 0.01 atmospheres and a pressure just below atmospheric pressure. Most preferably, when ammonia is removed from the reaction vessel by conducting the reaction at less than atmospheric pressure, a reaction pressure between about 0.01 and about 0.25 atmospheres is used.

The reaction time used in the practice of the present invention is of course dependent on the temperature, but preferably ranges between about 5 minutes and about 4 hours. Shorter and longer reaction times may be used if desired. Preferably, the reaction time used is between about 15 minutes and about 2 hours.

The concentration of urea, biuret or a mixture of urea and biuret in a molten salt solution prior to conversion to cyanuric acid is preferably not so high that the amount of ammeline in the cyanuric acid product significantly increases. At very low concentrations, biuret or mixtures of urea and biuret, a very pure cyanuric acid product is obtained, although the costs per unit product obtained are high. Therefore, in order to obtain a pure cyanuric acid product at a suitable cost, it is preferred that the starting concentration of urea, biuret or mixtures of urea and biuret be in the range between about 150 and about 500 grams per kilogram of solution.

In the practice of the present invention, when urea, biuret or a mixture of urea and biuret is heated in a molten salt solvent as described above, a cyanuric acid product is formed which is relatively insoluble in the molten salt solvent and forms a crystalline precipitate in the molten salt solvent. The cyanuric acid product may be separated from the molten salt solvent by conventional techniques.

In the practice of the present invention, it is found that a pure cyanuric acid product with a low content of ammelide and ammeline is obtained. It is also to be noted that the pure cyanuric acid product contains little or no guanidine nitrate as a by-product, generally less than 1% by weight.

The invention will now be elucidated in more detail in the following Examples.

EXAMPLES I TO III AND COMPARATIVE EXPERIMENTS A AND B

A mixture of the specified amount of urea and the specified amounts of the salts indicated was heated from room temperature to the specified reaction temperature in a 250-ml flask with proper stirring, while the specified amount (expressed in normal liters, abbreviated Nl, per hour) of stripping gas was passed through the reaction flask. Nitrogen was used as the stripping gas in Examples I, II and III and Comparative Experiment B. No stripping gas was used in Comparative Experiment A. The reaction time was measured from the time the reaction temperature was reached. At the end of the reaction time specified, the reaction mixture was rapidly cooled to room temperature by means of ice water. Salt(s) and unconverted urea were dissolved in water, the cyanuric acid was filtered off, washed with water and dried. The percentage of ammelide (including ammeline) was calculated with respect to the total amount of cyanuric acid formed.

In Comparative Experiment B the amount of ammonium nitrate used was insufficient to act as a solvent for the urea present. An ammonium nitrate solvent, as that term is used herein, means that the concentration of urea and/or biuret must be kept below 500 grams per kg of solution. It is noted that the ammelide content of the product of Comparative Experiment B is high, and the yield of cyanuric acid is correspondingly poor.

| Example | Urea (g) | NH$_4$NO$_3$ (g) | NaNO$_3$ (g) | Reaction Time (min) | Temperature (° C) | N$_2$ (Nl/h) | Urea Conversion % | Ammelide (% by weight) |
|---|---|---|---|---|---|---|---|---|
| Example I | 30.0 | 100.0 | — | 60 | 175 | 80 | 21 | 0.03 |
| Example II | 45.0 | 100.0 | — | 60 | 200 | 80 | 88 | 0.34 |
| Example III | 30.0 | 40.0 | 30.7 | 120 | 176 | about 80; not measured | 50 | 0.30 |
| Comparative Experiment A | 25.0 | 70.7 | — | 275 | 178 | 0 | 13 | not determined |
| Comparative Experiment B | 75.0 | 25.0 | — | 60 | 200 | 80 | 86 | 3.20 |

Thus, it is apparent that there has been provided in accordance with the invention, a process for preparing cyanuric acid by heating urea, or biuret or a mixture thereof in a molten salt solvent that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the following claims.

What is claimed is:

1. A process for preparing cyanuric acid, comprising:
   heating a solution of urea, biuret or a mixture of urea and biuret in a molten salt solvent comprising ammonium nitrate, wherein the concentration of urea and/or biuret is kept below 500 grams per kg of solution.
   forming cyanuric acid and ammonia in said solution, and
   reducing during the reaction the concentration of said ammonica in said solution.

2. The process according to claim 1 wherein said molten salt solvent contains at least one salt other than ammonium nitrate, said salt being present in an amount up to 50% by weight based on the weight of the solvent.

3. The process according to claim 2 wherein said salt other than ammonium nitrate is an alkali metal salt, an alkaline earth metal salt, or an ammonium salt.

4. The process according to claim 3 wherein said salt is an alkali metal nitrate or an alkaline earth metal nitrate.

5. The process according to claim 4 wherein said molten salt solvent is a mixture of ammonium nitrate and sodium nitrate, or ammonium nitrate and potassium nitrate.

6. The process according to claim 1 including heating said solution of urea, biuret or a mixture of urea and biuret in said molten salt solvent at a temperature from 150° C to 280° C.

7. The process according to claim 1 including heating said solution of urea, biuret or a mixture of urea and biuret in said molten salt solvent at a temperature from 170° C to 220° C.

8. The process according to claim 1 wherein ammonia is removed from said solution containing cyanuric acid by stripping with a stripping gas, a stripping additive or a mixture of a stripping gas and a stripping additive.

9. The process according to claim 1 wherein ammonia is removed by heating said solution of urea, biuret or a mixture of urea and biuret in a molten salt solvent under less than atmospheric pressure.

* * * * *